United States Patent [19]

Shafir

[11] Patent Number: 4,852,929
[45] Date of Patent: Aug. 1, 1989

[54] FREE STANDING TWEEZER

[76] Inventor: Grace C. Shafir, 36 Jane Dr., Englewood Cliffs, N.J. 07632

[21] Appl. No.: 224,056

[22] Filed: Jul. 25, 1988

[51] Int. Cl.⁴ .............................................. B65G 7/12
[52] U.S. Cl. ................................... 294/99.2; 128/354
[58] Field of Search ...................... 294/99.2, 1.1, 1.2, 294/25, 26, 27.1, 33; 128/354, 346

[56] References Cited

U.S. PATENT DOCUMENTS 3,744,883  7/1973  Williams .............................. 128/354

FOREIGN PATENT DOCUMENTS 523801  5/1957  Italy .................................... 294/99.2

Primary Examiner—James B. Marbert
Attorney, Agent, or Firm—Ostrolenk, Faber, Gerb & Soffen

[57] ABSTRACT

A tweezer is constructed so that it is free standing in a vertical position with its gripping end positioned upward.

8 Claims, 1 Drawing Sheet

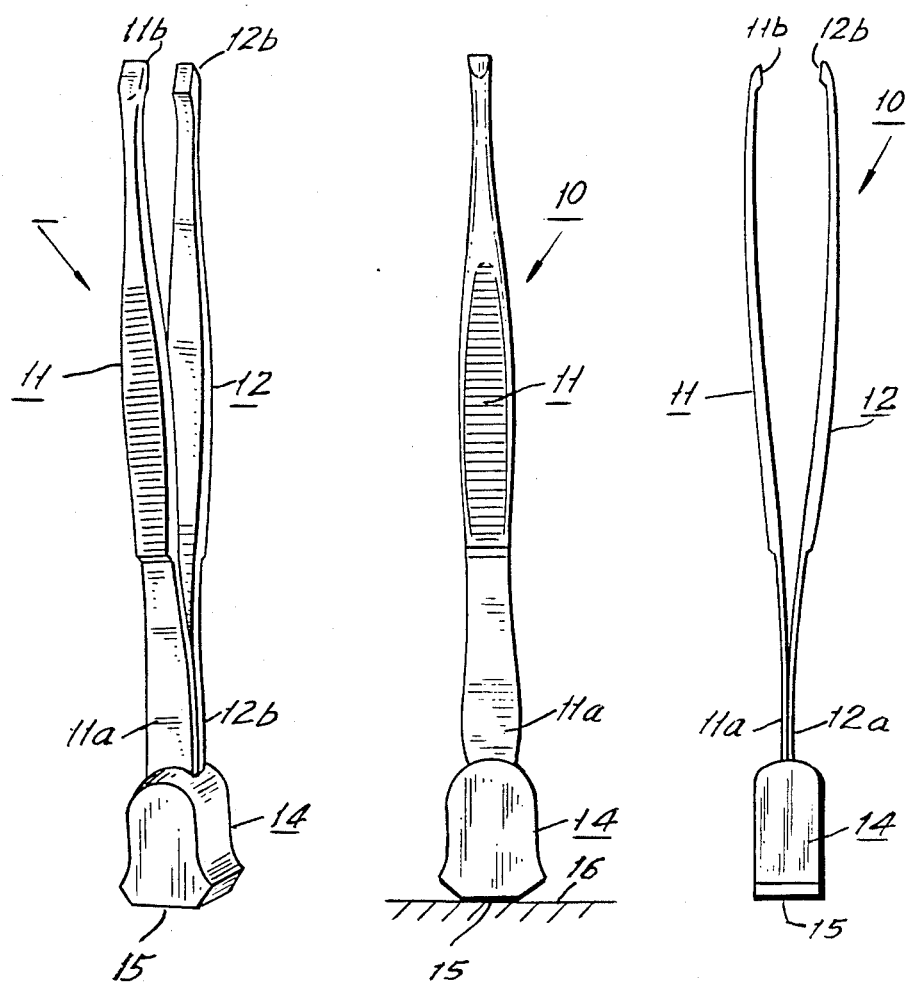
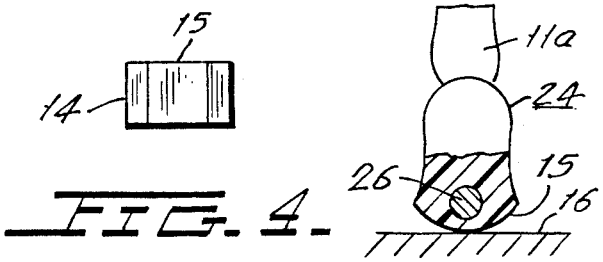

FREE STANDING TWEEZER

BACKGROUND OF THE INVENTION

This invention relates to pincer-like tools in general and more particularly relates to a tweezer that is free standing in an upright position.

A tweezer for cosmetic purposes is often used to grasp a particular strand of hair or other very small objects that are difficult to see, especially if the small object to be grasped is near an eye of the user and the user is unable to view the small object with both eyes. Under such circumstances after the object is located it should not be lost from view even momentarily. The latter condition gives rise to the need for having a tweezer in a position that will enable it to be located readily without interrupting sighting on the object to be grasped.

Unfortunately, in the prior art this was difficult to achieve because a tweezer was usually mingled with other implements from which a tweezer was not easily distinguished merely by touch.

BRIEF DESCRIPTION OF THE INVENTION

To alleviate the foregoing condition the tweezer of the instant invention is provided with means whereby the tweezer is free standing in an upright position so that it is readily distinguished from other implements merely by feel. This is achieved by providing an enlargement in the form of a block disposed at the end of the tweezer where the arms thereof are joined together. This block includes a flat surface which is positioned so that when it rests upon a horizontal support surface, the tweezer extends vertically upward therefrom as distinguished from the other implements that are horizontal. The block also facilitates grasping of the tweezer.

In another embodiment of this invention the block is provided with an arcuate surface and a weight means which is so positioned that when the arcuate surface rests upon a horizontal support surface gravity automatically directs the tweezer arms to a vertically upward position.

Because the tweezer of this invention stands vertically, it is more easily located by both sight and feel. Further, standing the tweezer vertically on a wet surface, as is often found adjacent to a sink, will wet only a small portion of the tweezer, whereas extensive areas of a tweezer lying down, as in the prior art, will get wet causing the metal plating thereon to rust.

Accordingly, the primary object of the instant invention is to provide a novel construction for a tweezer which facilitates locating same.

Another object is to provide a tweezer that is free standing in a vertical position.

Still another object is to provide a tweezer that is readily located even without the benefit of a clear visual sighting.

A further object is to provide a free standing tweezer that includes a block disposed opposite the grasping surfaces of the tweezer and is provided with an appropriately shaped surface that rests upon a horizontal support surface to position the arms of the tweezer so that they project vertically upward.

A still further object is to provide a tweezer having improved hygienic qualities and is easy to grasp.

BRIEF DESCRIPTION OF THE DRAWINGS

These objects as well as other objects of this invention shall become readily apparent after reading the following description of the accompanying drawings in which:

FIG. 1 is a perspective of a free standing tweezer constructed in accordance with teachings of the instant invention.

FIG. 2 is a front elevation of the tweezer of FIG. 1;

FIG. 3 is a side elevation of the tweezer;

FIG. 4 is a bottom view of the tweezer; and

FIG. 5 is a fragmentary front elevation constructed according to another embodiment of the instant invention.

DETAILED DESCRIPTION OF THE INVENTION

Now referring to the Figures and more particularly to FIGS. 1 through 4 which illustrate free standing tweezer 10 constructed in accordance with the first embodiment of the instant invention. Tweezer 10 includes first and second elongated arms 11, 12 that are constructed of resilient metal. Arms 11, 12 extend alongside one another with their lower ends 11a, 12a respectively being connected and extending into block 14. The upper ends of arms 11, 12 are provided with confronting gripping surfaces 11b, 12b, respectively, between which an object is grasped by tweezer 10. Gripping surfaces 11b, 12b are biased apart to the normally open position of tweezer 10 illustrated in FIG. 3. Block 14 is provided with flat support surface 15. When the latter rests upon horizontal supporting surface 16, arms 11, 12 extend vertically upward so that tweezer 10 may be readily located merely be feeling for same. Block 14 is constructed of metal or plastic.

In the second embodiment of this invention illustrated in FIG. 5, block 14 is replaced by block 24 having concentrated weight 26 embedded therein close to the center or lowest point of arcuate support surface 15. The latter may be spherically shaped or be another curved surface of revolution formed about a vertical axis. Surface 15 may also have an arcuate shape that is the same for all locations along a horizontal axis. The location of weight 26, its size and its weight in proportion to that of arms 11 and 12 are such that, through the action of gravity, when arcuate surface 15 is placed on supporting surface 16 block 24 is caused to oscillate until it automatically assumes an equilibrium position in which the tweezer arms 11, 12 extend generally vertically upward.

While the foregoing description makes reference to a tweezer used for cosmetic purposes, this type of tweezer is also useful for many other purposes, such as for medical purposes, say to remove splinters and stitches. Gemologists use a tweezer to handle gemstones, assemblers and service personnel for electronic and optical equipment use tweezers to handle small delicate components, and persons engaged in the field of microtechnology use tweezers for grasping minute elements.

Although the present invention has been described in connection with a plurality of preferred embodiments thereof, many other variations and modifications will now become apparent to those skilled in the art. It is preferred, therefore, that the present invention be limited not by the specific disclosure herein, but only by the appended claims.

What is claimed is:

1. A free standing tweezer including:
   confronting first and second elongated arms each having a first end and a second end opposite said first end;
   said arms being joined at said first ends;
   said second ends including gripping surfaces between which articles are grasped;
   biasing means urging said gripping surfaces apart;
   a block unit at said first ends interposed between said arms and a horizontal surface on which said tweezer is supported;
   said block unit being constructed to engage and cooperate with a horizontal surface to maintain said arms extending upward therefrom;
   said block unit including an arcuate surface and weight means operatively disposed so that with said arcuate surface resting on a horizontal supporting surface, gravity acts on said weight means to automatically position the tweezer with said arms projecting generally vertically upward.

2. A free standing tweezer as set forth in claim 1 in which the arcuate surface is a curved surface of revolution formed about a vertical axis.

3. A free standing tweezer as set forth in claim 1 in which the curved surface of revolution is spherical.

4. A free standing tweezer as set forth in claim 1 in which the weight means is embedded in the block unit vary close to the lowest portion of the arcuate surface.

5. A free standing tweezer including:
   confronting first and second elongated arms each having a first end and a second end opposite said first end;
   said arms being joined at said first ends which abut one another;
   said second ends including gripping surfaces between which articles are grasped;
   biasing means urging said gripping surfaces apart;
   a block unit at said first ends interposed between said arms and a horizontal surface on which said tweezer is supported;
   said block unit being constructed to engage and cooperate with a horizontal surface to maintain said arms extending upward therefrom.

6. A free standing tweezer as set forth in claim 5 in which the block unit is a solid member.

7. A free standing tweezer as set forth in claim 6 in which the block unit includes a flat support surface operatively positioned to engage a horizontal surface on which the tweezer is supported, with said arms projecting generally vertically upward therefrom.

8. A free standing tweezer as set forth in claim 5 in which the block unit includes a flat support surface operatively positioned to engage a horizontal surface on which the tweezer is supported, with said arms projecting generally vertically upward therefrom.

* * * * *